US011246810B2

United States Patent
Metten et al.

(10) Patent No.: US 11,246,810 B2
(45) Date of Patent: Feb. 15, 2022

(54) SPRAYABLE COSMETIC AGENT II

(71) Applicant: Henkel AG & Co. KGaA, Duesseldorf (DE)

(72) Inventors: Diane Metten, Hamburg (DE); Rene Scheffler, Ellerau (DE); Julia Bibiane Lange, Bad Bramstedt (DE); Cyrielle Martinez, Hamburg (DE); Thorsten Knappe, Schenefeld (DE); Rolf Bayersdoerfer, Hamburg (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 234 days.

(21) Appl. No.: 16/498,298

(22) PCT Filed: Mar. 9, 2018

(86) PCT No.: PCT/EP2018/055892
§ 371 (c)(1),
(2) Date: Sep. 26, 2019

(87) PCT Pub. No.: WO2018/177721
PCT Pub. Date: Oct. 4, 2018

(65) Prior Publication Data
US 2020/0030196 A1 Jan. 30, 2020

(30) Foreign Application Priority Data

Mar. 31, 2017 (DE) .................. 10 2017 205 556.1
Nov. 21, 2017 (DE) .................. 10 2017 220 775.2

(51) Int. Cl.
*A61K 8/27* (2006.01)
*A61K 8/02* (2006.01)
*A61K 8/04* (2006.01)
*A61K 8/34* (2006.01)
*A61K 8/73* (2006.01)
*A61Q 5/02* (2006.01)
*A61Q 5/06* (2006.01)
*B65D 83/14* (2006.01)

(52) U.S. Cl.
CPC ............. *A61K 8/027* (2013.01); *A61K 8/046* (2013.01); *A61K 8/34* (2013.01); *A61K 8/731* (2013.01); *A61K 8/732* (2013.01); *A61Q 5/02* (2013.01); *A61Q 5/06* (2013.01); *A61K 2800/412* (2013.01); *A61K 2800/432* (2013.01); *B65D 83/14* (2013.01)

(58) Field of Classification Search
CPC ...................................................... A61K 8/027
See application file for complete search history.

(56) References Cited

U.S. PATENT DOCUMENTS

| 4,966,607 A * | 10/1990 | Shinoki .................. C08B 31/00 536/45 |
| 5,965,146 A | 10/1999 | Franzke et al. |
| 6,342,237 B1 * | 1/2002 | Bara ........................ A61Q 1/02 424/401 |
| 2007/0011821 A1 * | 1/2007 | Pasquier ................... D06P 1/08 8/405 |
| 2012/0282190 A1 | 11/2012 | Hammer |

FOREIGN PATENT DOCUMENTS

| DE | 19640099 A1 | 4/1998 |
| JP | H11 158034 A | 6/1999 |
| WO | 2017178855 A1 | 10/2017 |

OTHER PUBLICATIONS

EPO, International Search Report issued in International Application No. PCT/EP2018/055892, dated Apr. 27, 2018.
Anonymous: "D.S.A 7 RED", XP55469654, Retrieved from the Internet: URL:http://www.agrana.com/fileadmin/inhalte/agrana_group/2017/images/Starch/Folder/Kosmetik/PDB_D.S.A.7_9017_en.pdf, Oct. 4, 2016, [retrieved on Apr. 23, 2018] the whole document.
Anonymous: "Dry Shampoo black & conditioner with D.S.A.7 black 20%", XP55469665, Retrieved from the Internet: URL:https://services.agrana.com/fileadmin/inhalte/austria/products/Kosmetik_Formulierungen/2018_Kosmetikdatein_Download/2018_Formulierungen/AGRANA_-_Dry_Shampoo_black_and_conditioner_with_D.S.A._7_black_20.pdf, Dec. 5, 2016, [retrieved on Apr. 23, 2018] the whole document.

* cited by examiner

*Primary Examiner* — Benjamin J Packard
(74) *Attorney, Agent, or Firm* — Lorenz & Kopf, LLP

(57) ABSTRACT

Cosmetic composition for cosmetic treatment of keratinous fibers, comprising:
(a) from about 0.1 to about 5.0 wt % fibers
(b) from about 5.0 to about 19 wt % ethanol
(c) from about 78 to about 94 wt % propellant.

20 Claims, No Drawings

SPRAYABLE COSMETIC AGENT II

CROSS-REFERENCE TO RELATED APPLICATION

This application is a U.S. National-Stage entry under 35 U.S.C. § 371 based on International Application No. PCT/EP2018/055892, filed Mar. 9, 2018, which was published under PCT Article 21(2), which claims priority to German Application No. 10 2017 220 775.2, filed Nov. 21, 2017, and which claims priority to German Application No. 10 2017 205 556.1, filed Mar. 31, 2017, which are all hereby incorporated in their entirety by reference.

TECHNICAL FIELD

The present disclosure relates to sprayable cosmetic compositions for treating keratinous fibers which also contain fibers besides a solvent and a propellant. These products lend are suitable for a wide variety of cosmetic purposes, including cleaning, reviving and deodorizing keratinous fibers.

BACKGROUND

Nowadays, an elegant hairstyle is generally considered to be an indispensable element of a well-groomed appearance. An aspect of hair care is reviving and cleaning the hair.

In the realm of cleaning, reviving and deodorizing keratin-containing fibers, the sprayed application of solid cosmetic agents has some degree of importance. As a rule, these agents are starch or starch derivatives, which are applied to the hair as an component of dry shampoos and then either left in the hair or brushed out.

As with other sprayed applications as well, a disadvantage of the sprayed application of dry shampoos containing solids is the technical difficulty of guaranteeing that the sprayed cosmetic will be spread evenly. To solve this problem in the past, various configurations particularly of the spray apparatus including the spray head have been described.

BRIEF SUMMARY

This disclosure provides a cosmetic composition for cosmetic treatment of keratinous fibers. The composition includes: (a) from about 0.1 to about 5.0 wt % fibers; (b) from about 5.0 to about 19 wt % ethanol; and (c) from about 78 to about 94 wt % propellant.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The present disclosure further relates to the cosmetic use of said products and hair grooming methods using said products.

In this context, the object of the present disclosure was to provide sprayable hair cosmetics which are exemplified by improved application properties, in particular an improved spray pattern compared with conventional preparations. It was found that this object may be solved by the addition of fibers to the sprayable cosmetic preparations.

With the present disclosure, the following is provided:

A cosmetic composition for the cosmetic treatment of keratinous fibers, comprising—relative to the total weight thereof—:
(a) from about 0.1 to about 5.0 wt % fibers
(b) from about 5.0 to about 19 wt % ethanol
(c) from about 78 to about 94 wt % propellant.

The cosmetic composition as contemplated herein, wherein it further contains
(d) from about 0 to about 5 wt % dye(s)
(e) from about 0 to about 5 wt % pigment(s)
with the qualification that the sum of the quantities of the substances (d) and (e) is equal to from about 0.0001 to about 10 wt % relative to the total weight of the cosmetic composition.

The cosmetic composition as contemplated herein, wherein the proportion by weight of the fibers is from about 0.1 to about 2.0 wt %, preferably from about 0.1 to about 1.0 wt % and particularly from about 0.1 to about 0.5 wt % relative to the total weight of the cosmetic composition.

The cosmetic composition as contemplated herein, wherein the fibers are selected from the group of fibers manufactured from natural fiber materials.

The cosmetic composition as contemplated herein, wherein the fibers are selected from the group of plant fibers, particularly cellulose fibers, preferably cotton fibers, flax fibers and kapok fibers.

The cosmetic composition as contemplated herein, wherein the fibers are selected from the group of animal fibers, preferably silk fibers, cashmere fibers and wool fibers.

The cosmetic composition as contemplated herein, wherein the fibers are selected from the group of fibers manufactured from synthetic fiber materials.

The cosmetic composition as contemplated herein, wherein the fibers are selected from the group of polyamide fibers, polyester fibers, polylactic acid fibers and polyhydroxyalkanoate fibers.

The cosmetic composition as contemplated herein, wherein the fibers have a length from about 1.0 to about 200 µm, preferably from about 2.0 to about 150 µm and particularly from about 5.0 to about 100 µm.

The cosmetic composition as contemplated herein, wherein the proportion by weight of the ethanol is from about 7.0 to about 17 wt %, preferably from about 9.0 to about 15 wt % and particularly from about 10 to about 14 wt % of the total weight of the cosmetic composition.

The cosmetic composition as contemplated herein, wherein the proportion by weight of the propellant is from about 82 to about 92 wt %, preferably from about 84 to about 90 wt % of the total weight of the cosmetic composition.

The cosmetic composition as contemplated herein, wherein the composition comprises a propellant from the group of propane, propane/butane mixtures and dimethyl ether, particularly from the group of propane/butane mixtures.

The cosmetic composition as contemplated herein, wherein the composition comprises at least one starch compound as a further constituent.

The cosmetic composition as contemplated herein, wherein the composition comprises a starch compound which constitutes from about 1.0 to about 10 wt %, preferably from about 2.0 to about 6.0 wt % and particularly from about 3.0 to about 5.0 wt % relative to the total weight thereof.

The cosmetic composition as contemplated herein, wherein the composition comprises a starch compound from the group of potatoes, corn, rice, peas, acorns, chestnuts, barley, wheat, bananas, sago, millet, sorghum, oats, barley, rye, beans, batata, arrowroot or manioc, particularly from the group of rice starches.

The cosmetic composition as contemplated herein, wherein the fibers are hydrophobized.

The cosmetic composition as contemplated herein, wherein the fibers have an oil absorption capacity (about 20° C.) from about 0.2 to about 0.8 g jojoba oil/g, preferably from about 0.3 to about 0.7 g jojoba oil/g, particularly preferably from about 0.4 to about 0.6 g jojoba oil/g.

The cosmetic composition as contemplated herein, wherein the composition contains at least one tenside as a further constituent.

The cosmetic composition as contemplated herein, wherein the composition comprises from about 0.05 to about 2.0 wt %, preferably from about 0.1 to about 1.5 wt % and particularly from about 0.2 to about 1.0 wt % tenside relative to the total weight thereof.

The cosmetic composition as contemplated herein, wherein the fibers are hydrophilized.

The cosmetic composition as contemplated herein, wherein the fibers have a water adsorption capacity (about 20° C.) greater than about 5.0 wt %, preferably greater than about 7.0 wt % and particularly greater than about 9.0 wt % relative to their dead weight.

The cosmetic composition as contemplated herein, wherein the composition comprises at least one cooling agent as a further constituent.

The cosmetic composition as contemplated herein, wherein the composition comprises from about 0.01 to about 1.0 wt %, preferably from about 0.02 to about 0.6 wt % and particularly from about 0.05 to about 0.4 wt % cooling agent relative to the total weight thereof.

The cosmetic composition as contemplated herein, wherein the composition comprises at least one fragrance as a further constituent.

The cosmetic composition as contemplated herein, wherein the composition comprises at least one polymer as a further constituent.

The cosmetic composition at contemplated herein, wherein the composition comprises at least one polymer from the group of copolymers of i) N-tert-octylacrylamide, ii) acrylic acid, iii) tert.-butylaminoethyl methacrylate and optionally further monomers as a further constituent.

The cosmetic composition as contemplated herein, wherein it contains from about 0.0001 to about 10 wt %, preferably from about 0.01 to about 9.5 wt %, more preferably from about 0.05 to about 9 wt %, still more preferably from about 0.1 to about 8.5 wt % and particularly from about 0.25 to about 8 wt % dye(s), relative in each case to the total weight thereof.

The cosmetic composition as contemplated herein, wherein it contains from about 0.0001 to about 10 wt %, preferably from about 0.01 to about 9.5 wt %, more preferably from about 0.05 to about 9 wt %, still more preferably from about 0.1 to about 8.5 wt % and particularly from about 0.25 to about 8 wt % pigment(s), relative in each case to the total weight thereof.

The cosmetic composition as contemplated herein, wherein it contains at least one pigment from the group CI12490, CI14700, CI14720, CI15510, CI15985, CI45380, CI47005, CI60730, CI61565, CI73360, CI74160, CI77007, CI77019, CI77288, CI77289, CI77491, CI77492, wherein the total quantity of pigment(s) from this group constitutes from about 0.0001 to about 10 wt %, preferably from about 0.01 to about 9.5 wt %, more preferably from about 0.05 to about 9 wt %, still more preferably from about 0.1 to about 8.5 wt % and particularly from about 0.25 to about 8 wt %, relative in each case to the total weight of the cosmetic composition.

The cosmetic composition as contemplated herein \, wherein it contains the substances (d) and/or (e) in the form of a starch-dye compound and/or a starch-pigment compound, preferably in the form of dyed and/or pigmented rice starch.

The cosmetic composition as contemplated herein, wherein it contains the substances (a) and (d) and/or (a) and (e) in the form of a fiber-dye compounds or a fiber-pigment compound, preferably in the form of dyed and/or pigmented fibers.

A cosmetic product, comprising
a) a cosmetic composition as contemplated herein
b) an aerosol dispensing container.

Use of a cosmetic composition as contemplated hereinfor cleaning keratinous fibers, particularly human hair.

The use of a cosmetic composition as contemplated hereinfor reviving keratinous fibers, particularly human hair.

The use of a cosmetic composition as contemplated hereinfor deodorizing keratinous fibers, particularly human hair.

A method for temporary reshaping of keratinous fibers, particularly human hair, in which the cosmetic composition as contemplated herein is applied to keratinous fibers.

The cosmetic composition contains fibers as its first constituent. The addition of these fibers influences the application properties of the sprayable hair cosmetic in an unexpected way. The spray pattern and the application of the sprayed cosmetic become more even. In a standardized test arrangement, with the same pressure in the spray apparatus and at the same distance from the surface to be sprayed, the addition of the fibers also resulted in a surprising increase in the area the spray reached.

Elongated, flexible structures of fibrous material with a length to diameter ratio greater than about 3:1, preferably greater than about 5:1 and particularly greater than about 10:1 are used as the fibers. Fibers can only withstand tensile forces, not compressive forces.

The length of fibers used for preference is in the range from about 1.0 to about 200 µm, preferably from about 2.0 to about 150 µm and particularly from about 5.0 to about 100 µm. Of course, however, fibers with longer fiber length may also be used, for example fibers with a length greater than about 200 µm or greater about 300 µm.

The fiber material may be of natural or synthetic origin. All fibers which are obtained from plant, animal or mineral material without chemical modification are classified as natural fibers.

Plant fibers occur in plants as vascular bundles in the stalk, the stem, in the bark or as seed pods. Plant fibers typically include mostly cellulose. Fibers of such kind are classified together under the term cellulose fibers.

According to a popular classification system, seed fibers are subdivided further into bast fibers, leaf fibers and fruit fibers. The group of seed fibers includes for example the cotton fibers, kapok, crown flower or populus seeds. The group of bast fibers includes bamboo fibers, nettles, hemp fibers, jute and flax fibers among others. On the other hand, sisal should be classified with the leaf fibers while coconut fibers belong to the group of fruit fibers.

With regard to the animal fibers, a distinction may be made between fibers from silk glands and fibers that originate from hair follicles. Fibers from silk glands include silk, for example. The of fibers that originate from hair follicles includes wool, alpaca, camelhair, angora, cashmere, mohair, yak hair, goat hair, cow hair or horse hair, among others.

In a preferred embodiment, the fibers used in the cosmetic compositions are chosen from the group of fibers from natural fiber materials. The use of cellulose fibers, particularly cotton fibers, flax fibers and kapok fibers is especially preferred. Particularly provided is the use of animal fibers from the group of silk fibers, cashmere fibers and wool fibers. The use of cellulose fibers is especially preferred.

Fibers based on synthetic fiber materials may also be used in the cosmetic compositions instead or together with the previously described natural fibers.

Particularly preferred is the use of synthetic fiber materials obtained by modification of plant or animal raw materials. The group of these preferred fibers includes for example fibers made from viscose, polylactic acid, alginate, chitin or chitosan.

Further preferred synthetic fiber materials are polyamides, polyesters and polyhydroxyalkanoates.

Proportions by weight from about 0.1 to about 2.0 wt %, preferably from about 0.1 to about 1.0 wt % and particularly from about 0.1 to about 0.5 wt % of the fibers in the total weight of the cosmetic composition have proven particularly advantageous for the technical and cosmetic effects.

As the second constituent, the cosmetic compositions contain ethanol. The proportion by weight of ethanol in the total weight of the cosmetic composition is preferably from about 7.0 to about 17 wt %, more preferably from about 9.0 to about 15 wt % and particularly from about 10 to about 14 wt %. The fibers are suspended in the ethanol.

A third constituent of the cosmetic compositions is the propellant. It has been found to be particularly advantageous from both a cosmetic and technical point of view if the proportion by weight of the propellant in the total weight of the composition is from about 82 to about 92 wt %, preferably from about 84 to about 90 wt %.

Preferred propellants (propellant gases) are selected from propane, propene, n-butane, iso-butane, iso-butene, n-pentane, pentene, iso-pentane, iso-pentene, methane, ethane, dimethylether, nitrogen, air, oxygen, nitrous oxide, dichlorofluoromethane, chlorodifluoromethane, chlorofluoromethane, 1,1,2,2-tetrachloro-1-fluoroethane, 1,1,1,2-tetrachloro-2-fluoroethane, 1,2,2-trichloro-1,1-difluoroethane, 1,1,2-trichloro-1,2-difluoroethane, 1,1,1-trichloro-2,2-difluoroethane, 2,2-dichloro-1,1,1-trifluoroethane, 1,2-dichloro-1,1,2-trifluoroethane, 2-chloro-1,1,1,2-tetrafluoroethane, 1-chloro-1,1,2,2-tetrafluoroethane, 1,1,2-trichloro-2-fluoroethane, 1,2-dichloro-1,2-difluoroethane, 1,2-dichloro-1,1-difluoroethane, 1-chloro-1,2,2-trifluoroethane, 2-chloro-1,1,1-trifluoroethane, 1-chloro-1,1,2-trifluoroethane, 1,2-dichloro-1-fluoroethane, 1,1-dichloro-1-fluoroethane, 2-chloro-1,1-difluoroethane, 1-chloro-1,1-difluoroethane, 1-chloro-2-fluoroethane, 1-chloro-1-fluoroethane, 2-chloro-1,1-difluoroethene, 1,1,1,3-tetrafluoroethane, heptafluoro-n-propane, perfluoroethane, monochlorodifluoromethane, 1,1-difluoroethane, either alone or in combination.

The use of propane, propane/butane mixtures or dimethylether is preferred, the use of propane/butane mixtures is particularly preferred.

The compositions of some preferred cosmetic compositions are listed in the following Summary 1 (proportions in wt % are relative to the total weight of the cosmetic composition).

|  | Formula 1 | Formula 2 | Formula 3 | Formula 4 | Formula 5 |
| --- | --- | --- | --- | --- | --- |
| Fibers | 0.1 to 5.0 | 0.1 to 2.0 | 0.1 to 2.0 | 0.1 to 1.0 | 0.1 to 0.5 |
| Ethanol | 5.0 to 19 | 5.0 to 19 | 7.0 to 17 | 9.0 to 15 | 9.0 to 14 |
| Propellant | 80 to 94 | 80 to 94 | 82 to 92 | 80 to 90 | 80 to 90 |
| Optional additives | to 100 | to 100 | to 100 | to 100 | to 100 |

|  | Formula 6 | Formula 7 | Formula 8 | Formula 9 | Formula 10 |
| --- | --- | --- | --- | --- | --- |
| Cellulose fibers | 0.1 to 5.0 | 0.1 to 2.0 | 0.1 to 2.0 | 0.1 to 1.0 | 0.1 to 0.5 |
| Ethanol | 5.0 to 19 | 5.0 to 19 | 7.0 to 17 | 9.0 to 15 | 9.0 to 14 |
| Propellant | 80 to 94 | 80 to 94 | 80 to 92 | 80 to 90 | 80 to 90 |
| Optional additives | to 100 | to 100 | to 100 | to 100 | to 100 |

|  | Formula 11 | Formula 12 | Formula 13 | Formula 14 | Formula 15 |
| --- | --- | --- | --- | --- | --- |
| Fibers with a fiber length between 1.0 and 200 μm | 0.1 to 5.0 | 0.1 to 2.0 | 0.1 to 2.0 | 0.1 to 1.0 | 0.1 to 0.5 |
| Ethanol | 5.0 to 19 | 5.0 to 19 | 7.0 to 17 | 9.0 to 15 | 9.0 to 14 |
| Propellant | 80 to 94 | 80 to 94 | 80 to 92 | 80 to 90 | 80 to 90 |
| Optional additives | to 100 | to 100 | to 100 | to 100 | to 100 |

|  | Formula 16 | Formula 17 | Formula 18 | Formula 19 | Formula 20 |
| --- | --- | --- | --- | --- | --- |
| Cellulose fibers with a fiber length between 1.0 and 200 μm | 0.1 to 5.0 | 0.1 to 2.0 | 0.1 to 2.0 | 0.1 to 1.0 | 0.1 to 0.5 |
| Ethanol | 5.0 to 19 | 5.0 to 19 | 7.0 to 17 | 9.0 to 15 | 9.0 to 14 |
| Propellant | 80 to 94 | 80 to 94 | 80 to 92 | 80 to 90 | 80 to 90 |
| Optional additives | to 100 | to 100 | to 100 | to 100 | to 100 |

|  | Formula 21 | Formula 22 | Formula 23 | Formula 24 | Formula 25 |
| --- | --- | --- | --- | --- | --- |
| Fibers | 0.1 to 5.0 | 0.1 to 2.0 | 0.1 to 2.0 | 0.1 to 1.0 | 0.1 to 0.5 |
| Ethanol | 5.0 to 19 | 5.0 to 19 | 7.0 to 17 | 9.0 to 15 | 9.0 to 14 |

-continued

|  | Formula 21 | Formula 22 | Formula 23 | Formula 24 | Formula 25 |
|---|---|---|---|---|---|
| Propane/Butane | 80 to 94 | 80 to 94 | 80 to 92 | 80 to 90 | 80 to 90 |
| Optional additives | to 100 | to 100 | to 100 | to 100 | to 100 |

|  | Formula 26 | Formula 27 | Formula 28 | Formula 29 | Formula 30 |
|---|---|---|---|---|---|
| Cellulose fibers | 0.1 to 5.0 | 0.1 to 2.0 | 0.1 to 2.0 | 0.1 to 1.0 | 0.1 to 0.5 |
| Ethanol | 5.0 to 19 | 5.0 to 19 | 7.0 to 17 | 9.0 to 15 | 9.0 to 14 |
| Propane/Butane | 80 to 94 | 80 to 94 | 80 to 92 | 80 to 90 | 80 to 90 |
| Optional additives | to 100 | to 100 | to 100 | to 100 | to 100 |

|  | Formula 31 | Formula 32 | Formula 33 | Formula 34 | Formula 35 |
|---|---|---|---|---|---|
| Fibers with a fiber length between 1.0 and 200 μm | 0.1 to 5.0 | 0.1 to 2.0 | 0.1 to 2.0 | 0.1 to 1.0 | 0.1 to 0.5 |
| Ethanol | 5.0 to 19 | 5.0 to 19 | 7.0 to 17 | 9.0 to 15 | 9.0 to 14 |
| Propane/Butane | 80 to 94 | 80 to 94 | 80 to 92 | 80 to 90 | 80 to 90 |
| Optional additives | to 100 | to 100 | to 100 | to 100 | to 100 |

|  | Formula 36 | Formula 37 | Formula 38 | Formula 39 | Formula 40 |
|---|---|---|---|---|---|
| Cellulose fibers with a fiber length between 1.0 and 200 μm | 0.1 to 5.0 | 0.1 to 2.0 | 0.1 to 2.0 | 0.1 to 1.0 | 0.1 to 0.5 |
| Ethanol | 5.0 to 19 | 5.0 to 19 | 7.0 to 17 | 9.0 to 15 | 9.0 to 14 |
| Propane/Butane | 80 to 94 | 80 to 94 | 80 to 92 | 80 to 90 | 80 to 90 |
| Optional additives | to 100 | to 100 | to 100 | to 100 | to 100 |

Particularly preferred cosmetic compositions contain at least one coloring compound from the group of dyes and/or pigments. In this respect, the cosmetic compositions contain
(d) 0 to about 10 wt % dye(s) and/or
(e) 0 to about 10 wt % pigment(s),
with the qualification that the total of the quantities of substances (d) and (e) amounts to from about 0.0001 to about 10 wt %.

In other words, the cosmetic compositions may contain 0 wt % dyes (in which case at least one pigment must be present in a quantity of at least about 0.0001 wt %), but the dye content may also be as high as about 10 wt % (in which case pigment cannot be present. Regardless of whether
only one dye,
several dyes,
only one pigment,
several pigments,
one dye and several pigments
several dyes and one pigment
several dyes and several pigments
are used, the total quantity of all dyes and pigments (also referred to as the total quantity of coloring constituents) used in the cosmetic composition amounts to from about 0.0001 to about 10 wt % relative to the total weight of the cosmetic composition.

Preferred cosmetic compositions contain from about 0.0001 to about 10 wt %, preferably from about 0.01 to about 9.5 wt %, more preferably from about 0.05 to about 9 wt %, still more preferably from about 0.1 to about 8,5 wt % and particularly from about 0.25 to about 8 wt % dyes relative in each case to the total weight of the cosmetic composition.

Dyes are coloring agents which—unlike pigments—are soluble in the application medium (such as water, oils or other solvents).

A dye or a mixture of dyes can be selected depending on the desired color, color intensity or fastness properties of the resulting coloring. For this purpose, all dyes that are usual and commercially available in the cosmetics sector can be used without difficulty within the scope of the present disclosure.

Cosmetic compositions that are also preferred contain from about 0.0001 to about 10 wt %, preferably from about 0.01 to about 9.5 wt %, more preferably from about 0.05 to about 9 wt %, still more preferably from about 0.1 to about 8.5 wt % and particularly from about 0.25 to about 8 wt % pigment(s), relative in each case to the total weight of the cosmetic composition.

In general, all types of water-insoluble pigments are suitable, for example natural inorganic pigments (also called mineral pigments). These pigments contain mainly sulfides and oxides. Examples of such pigments are ocher (Fe(OOH); Pigment Yellow 43), burnt sienna ($Fe_2O_3$; Pigment Red 102), umber ($Fe_2O_3 \times MnO_2$; Pigment Brown 7:x), cinnabar (β-HgS, PR 106), lapislazuli (Ultramarine, $Na_6Al_6Si_6O_{24} \times Na_2Sn$; Pigment Blue 29), azurite (basic copper carbonate, $Cu_3[OH/CO_3]_2$; PB 30), green earth (FeO-containing silicate; Pigment Green 23), malachite ($Cu_2[(OH)_2, CO_3]$) and coal black (carbon (graphite), Pigment Black 9). However, the use of synthetic inorganic pigments has proven advantageous with regard to avoiding undesirable visible residues or gray films and/or the water-resistant temporary discoloration or the fibers. Synthetic inorganic pigments are manufactured for example by chemical and/or physical conversion (digestion, precipitation, calcining). They include in particular
white pigments (titanium dioxide ($TiO_2$), Pigment White PW 6; zinc sulfide (ZnS), PW 7; zinc oxide (ZnO), PW 4; antimona white ($SB_2O_3$), PW 11; lithopone ($ZnS/BaSO_4$), PW 5; white lead ($2PbCO_3 \times Pb(OH)_2$), PW 1),
secondarily white filler materials (calcium carbonate, PW 18; talc, PW 26 and barium sulfate, PW 21);
black pigments (manganese black, spinel black and carbon black pigments (graphite-carbon);
luster pigments (absorption pigments, metal pigments or metal effect pigments and nacreous pigments) as well as inorganic chromatic pigments (iron oxide pigments, iron blue pigments, ultramarine pigments, and the lead chromate, chromium oxide, cadmium and bismuth vanadate pigments which are less suitable due to their toxicological properties).

Preferred synthetic inorganic pigments are metal pigments or metal effect pigments produced from powdery metals or metal alloys such as a Aluminum bronzes (metal: Al), gold bronzes (metal: Cu, Cu—Al— or Cu—Zn alloy), silver bronzes (metal: Cu—Zn—Ni), fire-colored bronzes (metal: oxidized Cu—Zn) and patent bronzes (metal: Cu—Zn—(Ni)+dye).

Further preferred synthetic inorganic pigments are nacreous pigments, which include several layers with different refractive indices. Examples of nacreous pigments of such kind are magnesium stearate, zinc stearate and lithium stearate or ethylene glycol distearate or polyethylene terephthalate, and nacreous pigments that include mica, titanium dioxide (titanium dioxide-mica), bismuth chloride oxide or guanine, and may also be covered with colored oxide layers (e.g., iron oxides or chromium oxides). Nacreous pigments based on mica and mica/metal oxide are particularly preferred nacreous pigments. Micas belong to the group of sheet silicates. The most important representatives of these silicates are muscovite, phlogopite, paragonite, biotite, lepidolite and margarite. In order to manufacture the nacreous pigment together with metal oxides, the mica—usually muscovite or phlogopite—is coated with a metal oxide. Suitable metal oxides include but are not limited to $TiO_2$, $Cr_2O_3$ and $Fe_2O_3$. Interference pigments and luster pigments are obtained as preferred nacreous pigments as contemplated herein by corresponding coating processes. These nacreous pigment types also have coloring effects in addition to a glittering optical effect. Moreover, the nacreous pigments that are usable as contemplated herein may further contain a color pigment which is not derived from a metal oxide.

Most particularly preferred nacreous pigments are pigment which are marketed by the company Merck under the trade name Colorona®, wherein the pigments Colorona® red-brown (from about 47-57 wt % Muscovit Mica ($KH_2(AlSiO_4)_3$), from about 43-50 wt % $Fe_2O_3$ (INCI: Iron Oxides CI 77491), <3 wt % $TiO_2$ (INCI: Titanium Dioxide CI 77891), Colorona® Blackstar Blue (from about 39-47 wt % Muscovit Mica ($KH_2(AlSiO_4)_3$), from about 53-61 wt % $Fe_3O_4$ (INCI: Iron Oxides CI 77499)), Colorona® Siena Fine (from about 35-45 wt % Muscovit Mica ($KH_2(AlSiO_4)_3$), from about 55-65 wt % $Fe_2O_3$ (INCI: Iron Oxides CI 77491)), Colorona® Aborigine Amber (from about 50-62 wt % Muscovit Mica ($KH_2(AlSiO_4)_3$), from about 36-44 wt % $Fe_3O_4$ (INCI: Iron Oxides CI 77499), from about 2-6 wt % $TiO_2$ (INCI: Titanium Dioxide CI 77891)), Colorona® Patagonian Purple (from about 42-54 wt % Muscovit Mica ($KH_2(AlSiO_4)_3$), from about 26-32 wt % $Fe_2O_3$ (INCI: Iron Oxides CI 77491), from about 18-22 wt % $TiO_2$ (INCI: Titanium Dioxide CI 77891), from about 2-4 wt % Preussisch Blau (INCI: Ferric Ferrocyanide CI 77510)), Colorona® Chameleon (40-50 wt % Muscovit Mica ($KH_2(AlSiO_4)_3$), from about 50-60 wt % $Fe_2O_3$ (INCI: Iron Oxides CI 77491)) and Silk® Mica (>98 wt % Muscovit Mica ($KH_2(AlSiO_4)_3$)) are particularly preferred.

One group of particularly preferred pigments includes the coloring synthetic iron oxides. Particularly preferred representatives of this substance class are Pigment Brown 6 (CI No 77491), Pigment Red 101 (CI No 77491), Pigment Yellow 42 (CI No 77492), Pigment Black 11 (CI No 77499) and mixtures of said pigments.

Pigments that are most particularly preferred for use are exemplified by good sprayability in the compositions, a homogenous spray pattern and extremely low tendency to clog the spray nozzles. In this case, the most preferable cosmetic compositions contain at least one pigment from the group CI12490, CI14700, CI14720, CI15510, CI15985, CI45380, CI47005, CI60730, CI61565, CI73360, CI74160, CI77007, CI77019, CI77288, CI77289, CI77491, CI77492, wherein the total quantity of pigment(s) from this group is equal to from about 0.0001 to about 10 wt %, preferably from about 0.01 to about 9.5 wt %, more preferably from about 0.05 to about 9 wt %, still more preferably from about 0.1 to about 8.5 wt % and particularly from about 0.25 to about 8 wt %, relative to the total weight of the cosmetic composition in each case.

Preferred cosmetic compositions contain at least one starch compound as a further constituent. In this context, the term "starch" is understood to mean a reserve carbohydrate which is stored by many plants in the form of starch grains (granules) typically sized from about 1 to about 200 μm in various parts of the plant, e.g., in tubers or roots, crop seeds, fruits and in the pith.

The starch compound is preferably present as solid particles suspended in the ethanol. The term "solid particles" is understood to mean particulate that are solid at about 20° C. and about 1013.25 mbar.

A starch compound which is preferred for use as contemplated herein is selected from at least one—optionally modified—polycondensation product of D-Glucose obtained from the starch or potatoes, rice, corn, peas, acorns, chestnuts, barley, wheat, bananas, sago, millet, sorghum, oats, barley, rye, beans, batata, arrowroot or manioc. The composition as contemplated herein particularly preferably contains at least one starch compound which is or is derived from tapioca starch, potato starch, cornstarch or rice starch. Mixtures of said starch compounds also fall within the scope of the present disclosure.

Most particularly preferred is the use of rice starch. Starch compounds based on rice starch are available for example with the trade name Remy DR KA (INCI name: Oryza Sativa (Rice) Starch, CAS number 9005-25-8) from the company Bene O Remy Industries or with the name Rice Starch D.S.A. 7 (INCI name: Oryza Sativa (Rice) Starch, Cetrimonium Chloride; CAS number 9005-25-8) from the company Agrana.

Regarding cleaning performance, the use of native and/or physically modified rice starch has proven particularly advantageous. The term native is understood to refer to a starch which is isolated from starch-containing plants and which has not been physically or chemically modified after it has been isolated and purified. On the other hand, physically modified starch is understood to refer to a starch that has undergone at least a physical modification after isolation. In this context, physical modification with the application of pressure and/or heat and/or light. A modification by employing chemical and enzymatic reactions, for example hydrolysis the starch, does not fall with the mean of physical modification in this case. A physical modification that is used preferably is the application of heat, particularly boiling the native starch. Preferred embodiments of the present disclosure are therefore exemplified in that the compositions contain at least one starch selected from chemically and/or physically modified rice starches, particularly from physically modified rice starch. The use of native and/or physically modified rice starches in combination with dyes and/or pigments results in a particularly strong adhesion of the dyes and/or pigments to the starch, with the result that a long-lasting temporary hair coloring is enabled besides the excellent cleaning performance.

As a consequence, it is possible and preferable to use pre-dyed and/or pre-pigmented starches which are ideally suited for spraying with the cosmetic compositions. Particularly preferred cosmetic compositions contain the substance (d) and/or (e) in the form of a starch-dye compound and/or starch-pigment compound, preferably in the form of dyed and/or pigmented rice starch.

It has further been found that the composition of the starch particles itself has proven to contribute to the cosmetic effect. Accordingly, particles that are preferred for use include a certain proportion of native and/or physically modified starch, particularly rice starch. Thus it is preferable if the starch-dye compound and/or starch-pigment compound contains at least one starch, particularly a physically modified rice starch, in a total quantity from about 70 to about 96 wt %, particularly from about 80 to about 94 wt %, relative in each case to the total weight of the particle (compound). The use of particles that contain a high proportion by weight of physically modified rice starch results in particularly homogenous spray patterns and preferred adhesion of the dye to the keratinous fibers.

Naturally, the fibers of the cosmetic compositions may also be pre-dyed and/or pre-pigmented in addition to or instead of such compounds of starch and coloring substances. In this context, cosmetic compositions which contain the substances (a) and (d) and/or (a) and (e) in the form of a fiber-dye compound or fiber-pigment compound, preferably in the form of dyed and/or pigmented fibers, are particularly preferred.

The cosmetic effect and ease of application of the cosmetics may be influenced favorably by the starch content. Preferred cosmetic compositions comprises from about 1.0 to about 10 wt %, preferably from about 2.0 to about 6.0 wt % and particularly from about 3.0 to about 5.0 wt % of a starch compound relative to the total weight thereof.

The compositions of some preferred cosmetic compositions are listed in the following Summary 2 (proportions in wt % are relative to the total weight of the cosmetic composition).

|  | Formula 1 | Formula 2 | Formula 3 | Formula 4 | Formula 5 |
|---|---|---|---|---|---|
| Fibers | 0.1 to 5.0 | 0.1 to 2.0 | 0.1 to 2.0 | 0.1 to 1.0 | 0.1 to 0.5 |
| Starch compound | 1.0 to 10 | 1.0 to 10 | 2.0 to 6.0 | 2.0 to 6.0 | 3.0 to 5.0 |
| Ethanol | 5.0 to 19 | 5.0 to 19 | 7.0 to 17 | 8.0 to 15 | 8.0 to 12 |
| Propellant | 78 to 92 | 78 to 90 | 78 to 88 | 78 to 88 | 78 to 88 |
| Optional additives | to 100 | to 100 | to 100 | to 100 | to 100 |

|  | Formula 6 | Formula 7 | Formula 8 | Formula 9 | Formula 10 |
|---|---|---|---|---|---|
| Cellulose fibers | 0.1 to 5.0 | 0.1 to 2.0 | 0.1 to 2.0 | 0.1 to 1.0 | 0.1 to 0.5 |
| Starch compound | 1.0 to 10 | 1.0 to 10 | 2.0 to 6.0 | 2.0 to 6.0 | 3.0 to 5.0 |
| Ethanol | 5.0 to 19 | 5.0 to 19 | 7.0 to 17 | 8.0 to 15 | 8.0 to 12 |
| Propellant | 78 to 92 | 78 to 90 | 78 to 88 | 78 to 88 | 78 to 88 |
| Optional additives | to 100 | to 100 | to 100 | to 100 | to 100 |

|  | Formula 11 | Formula 12 | Formula 13 | Formula 14 | Formula 15 |
|---|---|---|---|---|---|
| Fibers with a fiber length between 1.0 and 200 μm | 0.1 to 5.0 | 0.1 to 2.0 | 0.1 to 2.0 | 0.1 to 1.0 | 0.1 to 0.5 |
| Starch compound | 1.0 to 10 | 1.0 to 10 | 2.0 to 6.0 | 2.0 to 6.0 | 3.0 to 5.0 |
| Ethanol | 5.0 to 19 | 5.0 to 19 | 7.0 to 17 | 8.0 to 15 | 8.0 to 12 |
| Propellant | 78 to 92 | 78 to 90 | 78 to 88 | 78 to 88 | 78 to 88 |
| Optional additives | to 100 | to 100 | to 100 | to 100 | to 100 |

|  | Formula 16 | Formula 17 | Formula 18 | Formula 19 | Formula 20 |
|---|---|---|---|---|---|
| Cellulose fibers with a fiber length between 1.0 and 200 μm | 0.1 to 5.0 | 0.1 to 2.0 | 0.1 to 2.0 | 0.1 to 1.0 | 0.1 to 0.5 |
| Starch compound | 1.0 to 10 | 1.0 to 10 | 2.0 to 6.0 | 2.0 to 6.0 | 3.0 to 5.0 |
| Ethanol | 5.0 to 19 | 5.0 to 19 | 7.0 to 17 | 8.0 to 15 | 8.0 to 12 |
| Propellant | 78 to 92 | 78 to 90 | 78 to 88 | 78 to 88 | 78 to 88 |
| Optional additives | to 100 | to 100 | to 100 | to 100 | to 100 |

|  | Formula 21 | Formula 22 | Formula 23 | Formula 24 | Formula 25 |
|---|---|---|---|---|---|
| Fibers | 0.1 to 5.0 | 0.1 to 2.0 | 0.1 to 2.0 | 0.1 to 1.0 | 0.1 to 0.5 |
| Starch compound | 1.0 to 10 | 1.0 to 10 | 2.0 to 6.0 | 2.0 to 6.0 | 3.0 to 5.0 |
| Ethanol | 5.0 to 19 | 5.0 to 19 | 7.0 to 17 | 8.0 to 15 | 8.0 to 12 |
| Propane/Butane | 78 to 92 | 78 to 90 | 78 to 88 | 78 to 88 | 78 to 88 |
| Optional additives | to 100 | to 100 | to 100 | to 100 | to 100 |

|  | Formula 26 | Formula 27 | Formula 28 | Formula 29 | Formula 30 |
|---|---|---|---|---|---|
| Cellulose fibers | 0.1 to 5.0 | 0.1 to 2.0 | 0.1 to 2.0 | 0.1 to 1.0 | 0.1 to 0.5 |
| Starch compound | 1.0 to 10 | 1.0 to 10 | 2.0 to 6.0 | 2.0 to 6.0 | 3.0 to 5.0 |
| Ethanol | 5.0 to 19 | 5.0 to 19 | 7.0 to 17 | 8.0 to 15 | 8.0 to 12 |

-continued

|  | | | | | |
|---|---|---|---|---|---|
| Propane/Butane | 78 to 92 | 78 to 90 | 78 to 88 | 78 to 88 | 78 to 88 |
| Optional additives | to 100 | to 100 | to 100 | to 100 | to 100 |

|  | Formula 31 | Formula 32 | Formula 33 | Formula 34 | Formula 35 |
|---|---|---|---|---|---|
| Fibers with a fiber length between 1.0 and 200 μm | 0.1 to 5.0 | 0.1 to 2.0 | 0.1 to 2.0 | 0.1 to 1.0 | 0.1 to 0.5 |
| Starch compound | 1.0 to 10 | 1.0 to 10 | 2.0 to 6.0 | 2.0 to 6.0 | 3.0 to 5.0 |
| Ethanol | 5.0 to 19 | 5.0 to 19 | 7.0 to 17 | 8.0 to 15 | 8.0 to 12 |
| Propane/Butane | 78 to 92 | 78 to 90 | 78 to 88 | 78 to 88 | 78 to 88 |
| Optional additives | to 100 | to 100 | to 100 | to 100 | to 100 |

|  | Formula 36 | Formula 37 | Formula 38 | Formula 39 | Formula 40 |
|---|---|---|---|---|---|
| Cellulose fibers with a fiber length between 1.0 and 200 μm | 0.1 to 5.0 | 0.1 to 2.0 | 0.1 to 2.0 | 0.1 to 1.0 | 0.1 to 0.5 |
| Starch compound | 1.0 to 10 | 1.0 to 10 | 2.0 to 6.0 | 2.0 to 6.0 | 3.0 to 5.0 |
| Ethanol | 5.0 to 19 | 5.0 to 19 | 7.0 to 17 | 8.0 to 15 | 8.0 to 12 |
| Propane/Butane | 78 to 92 | 78 to 90 | 78 to 88 | 78 to 88 | 78 to 88 |
| Optional additives | to 100 | to 100 | to 100 | to 100 | to 100 |

The fibers described in the introduction as the first constituent of the cosmetic compositions may be modified in various ways. Modifications of such kind relate for example to the length of the fibers or the ratio of their length to diameter as described earlier.

Another possible way to influence the technical and cosmetic properties of the compositions is to modify the surface properties of the fibers used.

In a first preferred embodiment, hydrophobized fibers are used. Hydrophobization (impregnation) lends the fibers a water-repellent shield. Paraffins or waxes, for example, but also film-forming silicones are suitable hydrophobizing agents.

Depending on the intended use of the cosmetic composition, it may be advantageous if the fibers have a certain oil absorption capacity. This oil absorption capacity may be influenced via the hydrophobization of the fibers described previously. The use of hydrophobized or non-hydrophobized fibers with an oil absorption capacity greater than about 0.2 g jojoba oil per gram fiber is preferred. Particularly preferred is the use of fibers with an oil absorption capacity (about 20° C.) from about 0.2 to about 0.8 g jojoba oil/g, preferably from about 0.3 to about 0.7 g jojoba oil/g, particularly preferably from about 0.4 to about 0.6 jojoba oil/g.

Among other effects of hydrophobizing the fibers, the sebum uptake capacity thereof is improved. Corresponding fibers are therefore used particularly in cosmetic compositions for cleaning purposes.

In order to enable an even suspension of the fibers in the cosmetic composition or to enhance the cosmetic effect of the composition for example, the compositions may comprise tenside as a further optional constituent. The use of non-ionic or cationic tensides is preferred.

Preferred cationic tensides are selected from the group of quarternary ammonium compounds. Preferred quaternary ammonium compounds are again ammonium halides, particularly chlorides and bromides, such as alkyltrimethyl ammonium chlorides, dialkyldimethyl ammonium chlorides and trialkyl methylammonium chlorides, e.g., cetyltrimethyl ammonium chloride, stearyl trimethyl ammonium chloride, distearyl dimethyl ammonium chloride, lauryl dimethyl ammonium chloride, lauryl dimethylbenzyl ammonium chloride and tricetylmethyl ammonium chloride, and the imidazolium compounds known by the INCI names Quaternium-27 and Quaternium-83. Most particularly preferred is the use of cetyl trimethyl ammonium chloride.

The tenside preferably constitutes a proportion by weight from about 0.05 to about 2.0 wt %, preferably from about 0.1 to about 1.5 wt % and particularly from about 0.2 to about 1.0 wt % of the total weight of the cosmetic composition.

The compositions of some further preferred cosmetic compositions are listed in the following Summary 3 (proportions in wt % are relative to the total weight of the cosmetic composition).

|  | Formula 1 | Formula 2 | Formula 3 | Formula 4 | Formula 5 |
|---|---|---|---|---|---|
| hydrophobized fibers | 0.1 to 5.0 | 0.1 to 2.0 | 0.1 to 2.0 | 0.1 to 1.0 | 0.1 to 0.5 |
| Ethanol | 5.0 to 19 | 5.0 to 19 | 7.0 to 17 | 9.0 to 15 | 9.0 to 14 |
| Propellant | 80 to 94 | 80 to 94 | 80 to 92 | 80 to 90 | 80 to 90 |
| Optional additives | to 100 | to 100 | to 100 | to 100 | to 100 |

|  | Formula 6 | Formula 7 | Formula 8 | Formula 9 | Formula 10 |
|---|---|---|---|---|---|
| hydrophobized cellulose fibers | 0.1 to 5.0 | 0.1 to 2.0 | 0.1 to 2.0 | 0.1 to 1.0 | 0.1 to 0.5 |
| Ethanol | 5.0 to 19 | 5.0 to 19 | 7.0 to 17 | 9.0 to 15 | 9.0 to 14 |
| Propellant | 80 to 94 | 80 to 94 | 80 to 92 | 80 to 90 | 80 to 90 |
| Optional additives | to 100 | to 100 | to 100 | to 100 | to 100 |

-continued

|  | Formula 11 | Formula 12 | Formula 13 | Formula 14 | Formula 15 |
|---|---|---|---|---|---|
| hydrophobized fibers with a fiber length between 1.0 and 200 μm | 0.1 to 5.0 | 0.1 to 2.0 | 0.1 to 2.0 | 0.1 to 1.0 | 0.1 to 0.5 |
| Ethanol | 5.0 to 19 | 5.0 to 19 | 7.0 to 17 | 9.0 to 15 | 9.0 to 14 |
| Propellant | 80 to 94 | 80 to 94 | 80 to 92 | 80 to 90 | 80 to 90 |
| Optional additives | to 100 | to 100 | to 100 | to 100 | to 100 |

|  | Formula 16 | Formula 17 | Formula 18 | Formula 19 | Formula 20 |
|---|---|---|---|---|---|
| hydrophobized cellulose fibers with a fiber length between 1.0 and 200 μm | 0.1 to 5.0 | 0.1 to 2.0 | 0.1 to 2.0 | 0.1 to 1.0 | 0.1 to 0.5 |
| Ethanol | 5.0 to 19 | 5.0 to 19 | 7.0 to 17 | 9.0 to 15 | 9.0 to 14 |
| Propellant | 80 to 94 | 80 to 94 | 80 to 92 | 80 to 90 | 80 to 90 |
| Optional additives | to 100 | to 100 | to 100 | to 100 | to 100 |

|  | Formula 21 | Formula 22 | Formula 23 | Formula 24 | Formula 25 |
|---|---|---|---|---|---|
| hydrophobized Fibers | 0.1 to 5.0 | 0.1 to 2.0 | 0.1 to 2.0 | 0.1 to 1.0 | 0.1 to 0.5 |
| Starch compound | 1.0 to 10 | 1.0 to 10 | 2.0 to 6.0 | 2.0 to 6.0 | 3.0 to 5.0 |
| Ethanol | 5.0 to 19 | 5.0 to 19 | 7.0 to 17 | 8.0 to 15 | 8.0 to 12 |
| Propellant | 78 to 92 | 78 to 90 | 78 to 88 | 78 to 88 | 78 to 88 |
| Optional additives | to 100 | to 100 | to 100 | to 100 | to 100 |

|  | Formula 26 | Formula 27 | Formula 28 | Formula 29 | Formula 30 |
|---|---|---|---|---|---|
| hydrophobized cellulose fibers | 0.1 to 5.0 | 0.1 to 2.0 | 0.1 to 2.0 | 0.1 to 1.0 | 0.1 to 0.5 |
| Starch compound | 1.0 to 10 | 1.0 to 10 | 2.0 to 6.0 | 2.0 to 6.0 | 3.0 to 5.0 |
| Ethanol | 5.0 to 19 | 5.0 to 19 | 7.0 to 17 | 8.0 to 15 | 8.0 to 12 |
| Propellant | 78 to 92 | 78 to 90 | 78 to 88 | 78 to 88 | 78 to 88 |
| Optional additives | to 100 | to 100 | to 100 | to 100 | to 100 |

|  | Formula 31 | Formula 32 | Formula 33 | Formula 34 | Formula 35 |
|---|---|---|---|---|---|
| hydrophobized Fibers with a fiber length between 1.0 and 200 μm | 0.1 to 5.0 | 0.1 to 2.0 | 0.1 to 2.0 | 0.1 to 1.0 | 0.1 to 0.5 |
| Starch compound | 1.0 to 10 | 1.0 to 10 | 2.0 to 6.0 | 2.0 to 6.0 | 3.0 to 5.0 |
| Ethanol | 5.0 to 19 | 5.0 to 19 | 7.0 to 17 | 8.0 to 15 | 8.0 to 12 |
| Propellant | 78 to 92 | 78 to 90 | 78 to 88 | 78 to 88 | 78 to 88 |
| Optional additives | to 100 | to 100 | to 100 | to 100 | to 100 |

|  | Formula 36 | Formula 37 | Formula 38 | Formula 39 | Formula 40 |
|---|---|---|---|---|---|
| hydrophobized cellulose fibers with a fiber length between 1.0 and 200 μm | 0.1 to 5.0 | 0.1 to 2.0 | 0.1 to 2.0 | 0.1 to 1.0 | 0.1 to 0.5 |
| Starch compound | 1.0 to 10 | 1.0 to 10 | 2.0 to 6.0 | 2.0 to 6.0 | 3.0 to 5.0 |
| Ethanol | 5.0 to 19 | 5.0 to 19 | 7.0 to 17 | 8.0 to 15 | 8.0 to 12 |
| Propellant | 78 to 92 | 78 to 90 | 78 to 88 | 78 to 88 | 78 to 88 |
| Optional additives | to 100 | to 100 | to 100 | to 100 | to 100 |

In an alternative embodiment, hydrophilized fibers are used in the cosmetic products. Corresponding fibers have a greater capacity to adsorb water than fibers which have not been hydrophilized.

The water adsorption capacity (about 20° C.) of preferred fibers, particularly preferred hydrophilized fibers, is preferably greater than about 5.0 wt %, preferably greater than about 7.0 wt % and particularly greater than about 9.0 wt % of the dead weight of the fibers.

One of the effects of hydrophilizing the fibers is that it improves their water uptake capacity. Corresponding fibers are therefore used particularly in revitalizing cosmetic compositions.

The compositions of some further preferred cosmetic compositions are listed in the following Summary 4 (proportions in wt % are relative to the total weight of the cosmetic composition).

|  | Formula 1 | Formula 2 | Formula 3 | Formula 4 | Formula 5 |
| --- | --- | --- | --- | --- | --- |
| hydrophilized fibers | 0.1 to 5.0 | 0.1 to 2.0 | 0.1 to 2.0 | 0.1 to 1.0 | 0.1 to 0.5 |
| Ethanol | 5.0 to 19 | 5.0 to 19 | 7.0 to 17 | 9.0 to 15 | 9.0 to 14 |
| Propellant | 80 to 94 | 80 to 94 | 80 to 92 | 80 to 90 | 80 to 90 |
| Optional additives | to 100 | to 100 | to 100 | to 100 | to 100 |

|  | Formula 6 | Formula 7 | Formula 8 | Formula 9 | Formula 10 |
| --- | --- | --- | --- | --- | --- |
| hydrophilized cellulose fibers | 0.1 to 5.0 | 0.1 to 2.0 | 0.1 to 2.0 | 0.1 to 1.0 | 0.1 to 0.5 |
| Ethanol | 5.0 to 19 | 5.0 to 19 | 7.0 to 17 | 9.0 to 15 | 9.0 to 14 |
| Propellant | 80 to 94 | 80 to 94 | 80 to 92 | 80 to 90 | 80 to 90 |
| Optional additives | to 100 | to 100 | to 100 | to 100 | to 100 |

|  | Formula 11 | Formula 12 | Formula 13 | Formula 14 | Formula 15 |
| --- | --- | --- | --- | --- | --- |
| hydrophilized fibers with a fiber length between 1.0 and 200 μm | 0.1 to 5.0 | 0.1 to 2.0 | 0.1 to 2.0 | 0.1 to 1.0 | 0.1 to 0.5 |
| Ethanol | 5.0 to 19 | 5.0 to 19 | 7.0 to 17 | 9.0 to 15 | 9.0 to 14 |
| Propellant | 80 to 94 | 80 to 94 | 80 to 92 | 80 to 90 | 80 to 90 |
| Optional additives | to 100 | to 100 | to 100 | to 100 | to 100 |

|  | Formula 16 | Formula 17 | Formula 18 | Formula 19 | Formula 20 |
| --- | --- | --- | --- | --- | --- |
| hydrophilized cellulose fibers with a fiber length between 1.0 and 200 μm | 0.1 to 5.0 | 0.1 to 2.0 | 0.1 to 2.0 | 0.1 to 1.0 | 0.1 to 0.5 |
| Ethanol | 5.0 to 19 | 5.0 to 19 | 7.0 to 17 | 9.0 to 15 | 9.0 to 14 |
| Propellant | 80 to 94 | 80 to 94 | 80 to 92 | 80 to 90 | 80 to 90 |
| Optional additives | to 100 | to 100 | to 100 | to 100 | to 100 |

|  | Formula 21 | Formula 22 | Formula 23 | Formula 24 | Formula 25 |
| --- | --- | --- | --- | --- | --- |
| hydrophilized fibers | 0.1 to 5.0 | 0.1 to 2.0 | 0.1 to 2.0 | 0.1 to 1.0 | 0.1 to 0.5 |
| Starch compound | 1.0 to 10 | 1.0 to 10 | 2.0 to 6.0 | 2.0 to 6.0 | 3.0 to 5.0 |
| Ethanol | 5.0 to 19 | 5.0 to 19 | 7.0 to 17 | 8.0 to 15 | 8.0 to 12 |
| Propellant | 78 to 92 | 78 to 90 | 78 to 88 | 78 to 88 | 78 to 88 |
| Optional additives | to 100 | to 100 | to 100 | to 100 | to 100 |

|  | Formula 26 | Formula 27 | Formula 28 | Formula 29 | Formula 30 |
| --- | --- | --- | --- | --- | --- |
| hydrophilized cellulose fibers | 0.1 to 5.0 | 0.1 to 2.0 | 0.1 to 2.0 | 0.1 to 1.0 | 0.1 to 0.5 |
| Starch compound | 1.0 to 10 | 1.0 to 10 | 2.0 to 6.0 | 2.0 to 6.0 | 3.0 to 5.0 |
| Ethanol | 5.0 to 19 | 5.0 to 19 | 7.0 to 17 | 8.0 to 15 | 8.0 to 12 |
| Propellant | 78 to 92 | 78 to 90 | 78 to 88 | 78 to 88 | 78 to 88 |
| Optional additives | to 100 | to 100 | to 100 | to 100 | to 100 |

|  | Formula 31 | Formula 32 | Formula 33 | Formula 34 | Formula 35 |
| --- | --- | --- | --- | --- | --- |
| hydrophilized fibers with a fiber length between 1.0 and 200 μm | 0.1 to 5.0 | 0.1 to 2.0 | 0.1 to 2.0 | 0.1 to 1.0 | 0.1 to 0.5 |
| Starch compound | 1.0 to 10 | 1.0 to 10 | 2.0 to 6.0 | 2.0 to 6.0 | 3.0 to 5.0 |
| Ethanol | 5.0 to 19 | 5.0 to 19 | 7.0 to 17 | 8.0 to 15 | 8.0 to 12 |
| Propellant | 78 to 92 | 78 to 90 | 78 to 88 | 78 to 88 | 78 to 88 |
| Optional additives | to 100 | to 100 | to 100 | to 100 | to 100 |

|  | Formula 36 | Formula 37 | Formula 38 | Formula 39 | Formula 40 |
| --- | --- | --- | --- | --- | --- |
| hydrophilized cellulose fibers with a fiber length between 1.0 and 200 μm | 0.1 to 5.0 | 0.1 to 2.0 | 0.1 to 2.0 | 0.1 to 1.0 | 0.1 to 0.5 |
| Starch compound | 1.0 to 10 | 1.0 to 10 | 2.0 to 6.0 | 2.0 to 6.0 | 3.0 to 5.0 |
| Ethanol | 5.0 to 19 | 5.0 to 19 | 7.0 to 17 | 8.0 to 15 | 8.0 to 12 |
| Propellant | 78 to 92 | 78 to 90 | 78 to 88 | 78 to 88 | 78 to 88 |
| Optional additives | to 100 | to 100 | to 100 | to 100 | to 100 |

In order to enhance the reviving effect of cosmetic compositions, at least one cooling agent may be added to them as a further optional constituent.

The group of cosmetically acceptable components which demonstrate a cooling effect includes substances which have a cooling effect through evaporation (e.g., isopropanol), or due to their effect on skin receptors. Examples of substances from this group are the compounds with INCI names Menthol, Menthyl Lactat, Menthone Glycerin Acetal and Methoxyphenyl Menthane Carboxamide. Menthyl Ethylamido Oxalate is available commercially under the trade name Frescolat® X-Cool (Symrise), for example.

The cooling agent preferably constitutes a proportion by weight from about 0.01 to about 1.0 wt %, preferably from about 0.02 to about 0.6 wt % and particularly from about 0.05 to about 0.4 wt % of the total weight of the cosmetic composition.

The compositions of some further preferred cosmetic compositions are listed in the following Summary 5 (proportions in wt % are relative to the total weight of the cosmetic composition).

|  | Formula 1 | Formula 2 | Formula 3 | Formula 4 | Formula 5 |
|---|---|---|---|---|---|
| Fibers | 0.1 to 5.0 | 0.1 to 2.0 | 0.1 to 2.0 | 0.1 to 1.0 | 0.1 to 0.5 |
| Cooling agent | 0.01 to 1.0 | 0.02 to 0.6 | 0.02 to 0.6 | 0.05 to 0.4 | 0.05 to 0.4 |
| Ethanol | 5.0 to 19 | 5.0 to 19 | 7.0 to 17 | 9.0 to 15 | 9.0 to 14 |
| Propellant | 80 to 94 | 80 to 94 | 80 to 92 | 80 to 90 | 80 to 90 |
| Optional additives | to 100 | to 100 | to 100 | to 100 | to 100 |

|  | Formula 6 | Formula 7 | Formula 8 | Formula 9 | Formula 10 |
|---|---|---|---|---|---|
| Cellulose fibers | 0.1 to 5.0 | 0.1 to 2.0 | 0.1 to 2.0 | 0.1 to 1.0 | 0.1 to 0.5 |
| Cooling agent | 0.01 to 1.0 | 0.02 to 0.6 | 0.02 to 0.6 | 0.05 to 0.4 | 0.05 to 0.4 |
| Ethanol | 5.0 to 19 | 5.0 to 19 | 7.0 to 17 | 9.0 to 15 | 9.0 to 14 |
| Propellant | 80 to 94 | 80 to 94 | 80 to 92 | 80 to 90 | 80 to 90 |
| Optional additives | to 100 | to 100 | to 100 | to 100 | to 100 |

|  | Formula 11 | Formula 12 | Formula 13 | Formula 14 | Formula 15 |
|---|---|---|---|---|---|
| Fibers with a fiber length between 1.0 and 200 μm | 0.1 to 5.0 | 0.1 to 2.0 | 0.1 to 2.0 | 0.1 to 1.0 | 0.1 to 0.5 |
| Cooling agent | 0.01 to 1.0 | 0.02 to 0.6 | 0.02 to 0.6 | 0.05 to 0.4 | 0.05 to 0.4 |
| Ethanol | 5.0 to 19 | 5.0 to 19 | 7.0 to 17 | 9.0 to 15 | 9.0 to 14 |
| Propellant | 80 to 94 | 80 to 94 | 80 to 92 | 80 to 90 | 80 to 90 |
| Optional additives | to 100 | to 100 | to 100 | to 100 | to 100 |

|  | Formula 16 | Formula 17 | Formula 18 | Formula 19 | Formula 20 |
|---|---|---|---|---|---|
| Cellulose fibers with a fiber length between 1.0 and 200 μm | 0.1 to 5.0 | 0.1 to 2.0 | 0.1 to 2.0 | 0.1 to 1.0 | 0.1 to 0.5 |
| Cooling agent | 0.01 to 1.0 | 0.02 to 0.6 | 0.02 to 0.6 | 0.05 to 0.4 | 0.05 to 0.4 |
| Ethanol | 5.0 to 19 | 5.0 to 19 | 7.0 to 17 | 9.0 to 15 | 9.0 to 14 |
| Propellant | 80 to 94 | 80 to 94 | 80 to 92 | 80 to 90 | 80 to 90 |
| Optional additives | to 100 | to 100 | to 100 | to 100 | to 100 |

|  | Formula 21 | Formula 22 | Formula 23 | Formula 24 | Formula 25 |
|---|---|---|---|---|---|
| Fibers | 0.1 to 5.0 | 0.1 to 2.0 | 0.1 to 2.0 | 0.1 to 1.0 | 0.1 to 0.5 |
| Starch compound | 1.0 to 10 | 1.0 to 10 | 2.0 to 6.0 | 2.0 to 6.0 | 3.0 to 5.0 |
| Cooling agent | 0.01 to 1.0 | 0.02 to 0.6 | 0.02 to 0.6 | 0.05 to 0.4 | 0.05 to 0.4 |
| Ethanol | 5.0 to 19 | 5.0 to 19 | 7.0 to 17 | 8.0 to 15 | 8.0 to 12 |
| Propellant | 78 to 92 | 78 to 90 | 78 to 88 | 78 to 88 | 78 to 88 |
| Optional additives | to 100 | to 100 | to 100 | to 100 | to 100 |

|  | Formula 26 | Formula 27 | Formula 28 | Formula 29 | Formula 30 |
|---|---|---|---|---|---|
| Cellulose fibers | 0.1 to 5.0 | 0.1 to 2.0 | 0.1 to 2.0 | 0.1 to 1.0 | 0.1 to 0.5 |
| Starch compound | 1.0 to 10 | 1.0 to 10 | 2.0 to 6.0 | 2.0 to 6.0 | 3.0 to 5.0 |
| Cooling agent | 0.01 to 1.0 | 0.02 to 0.6 | 0.02 to 0.6 | 0.05 to 0.4 | 0.05 to 0.4 |
| Ethanol | 5.0 to 19 | 5.0 to 19 | 7.0 to 17 | 8.0 to 15 | 8.0 to 12 |
| Propellant | 78 to 92 | 78 to 90 | 78 to 88 | 78 to 88 | 78 to 88 |
| Optional additives | to 100 | to 100 | to 100 | to 100 | to 100 |

|  | Formula 31 | Formula 32 | Formula 33 | Formula 34 | Formula 35 |
|---|---|---|---|---|---|
| Fibers with a fiber length between 1.0 and 200 μm | 0.1 to 5.0 | 0.1 to 2.0 | 0.1 to 2.0 | 0.1 to 1.0 | 0.1 to 0.5 |
| Starch compound | 1.0 to 10 | 1.0 to 10 | 2.0 to 6.0 | 2.0 to 6.0 | 3.0 to 5.0 |
| Cooling agent | 0.01 to 1.0 | 0.02 to 0.6 | 0.02 to 0.6 | 0.05 to 0.4 | 0.05 to 0.4 |
| Ethanol | 5.0 to 19 | 5.0 to 19 | 7.0 to 17 | 8.0 to 15 | 8.0 to 12 |

-continued

| | | | | | |
|---|---|---|---|---|---|
| Propellant | 78 to 92 | 78 to 90 | 78 to 88 | 78 to 88 | 78 to 88 |
| Optional additives | to 100 | to 100 | to 100 | to 100 | to 100 |

| | Formula 36 | Formula 37 | Formula 38 | Formula 39 | Formula 40 |
|---|---|---|---|---|---|
| Cellulose fibers with a fiber length between 1.0 and 200 μm | 0.1 to 5.0 | 0.1 to 2.0 | 0.1 to 2.0 | 0.1 to 1.0 | 0.1 to 0.5 |
| Starch compound | 1.0 to 10 | 1.0 to 10 | 2.0 to 6.0 | 2.0 to 6.0 | 3.0 to 5.0 |
| Cooling agent | 0.01 to 1.0 | 0.02 to 0.6 | 0.02 to 0.6 | 0.05 to 0.4 | 0.05 to 0.4 |
| Ethanol | 5.0 to 19 | 5.0 to 19 | 7.0 to 17 | 8.0 to 15 | 8.0 to 12 |
| Propellant | 78 to 92 | 78 to 90 | 78 to 88 | 78 to 88 | 78 to 88 |
| Optional additives | to 100 | to 100 | to 100 | to 100 | to 100 |

In a further alternative embodiment or in combination with the hydrophobized or hydrophilized fibers described earlier, preferred cosmetic compositions contain at least one fragrance.

Polymers may be used as the further optional constituent of the cosmetic composition. For the purposes of ease of application and the cosmetic effect of the compositions, it has proven to be advantageous to limit the proportion by weight of the polymer in the total weight of the composition to from about 0.1 to about 4.0 wt %, preferably from about 0.1 to about 2.0 wt % and particularly from about 0.1 to about 1.0 wt %.

Polymers are used in the cosmetic compositions for example due to their strengthening and/or film-forming properties. In view of their cosmetic effect, the use of film-forming polymers is particularly preferred.

Polymers suitable for such use are polymers that are both permanently and temporarily cationic, anionic, non-ionic or amphoteric. The film-forming polymers may be of synthetic or natural origin.

Examples of commonly used polymers are Acrylamide/Ammonium Acrylate Copolymer, Acrylamides/DMAPA Acrylates/Methoxy PEG Methacrylate Copolymer, Acrylamidopropyltrimonium Chloride/Acrylamide Copolymer, Acrylamidopropyltrimonium Chloride/Acrylates Copolymer, Acrylates/Acetoacetoxyethyl Methacrylate Copolymer, Acrylates/Acrylamide Copolymer, Acrylates/Ammonium Methacrylate Copolymer, Acrylates/t-Butylacrylamide Copolymer, Acrylates Copolymer, Acrylates/C1-2 Succinates/Hydroxyacrylates Copolymer, Acrylates/Lauryl Acrylate/Stearyl Acrylate/Ethylamine Oxide Methacrylate Copolymer, Acrylates/Octylacrylamide Copolymer, Acrylates/Octylacrylamide/Diphenyl Amodimethicone Copolymer, Acrylates/Stearyl Acrylate/Ethylamine Oxide Methacrylate Copolymer, Acrylates/VA Copolymer, Acrylates/VP Copolymer, Adipic Acid/Diethylenetriamine Copolymer, Adipic Acid/Dimethylaminohydroxypropyl Diethylenetriamine Copolymer, Adipic Acid/Epoxypropyl Diethylenetriamine Copolymer, Adipic Acid/Isophthalic Acid/Neopentyl Glycol/Trimethylolpropane Copolymer, Allyl Stearate/VA Copolymer, Aminoethylacrylate Phosphate/Acrylates Copolymer, Aminoethylpropanediol-Acrylates/Acrylamide Copolymer, Aminoethylpropanediol-AMPD-Acrylates/Diacetoneacrylamide Copolymer, Ammonium VA/Acrylates Copolymer, AMPD-Acrylates/Diacetoneacrylamide Copolymer, AMP-Acrylates/Allyl Methacrylate Copolymer, AMP-Acrylates/C1-18 Alkyl Acrylates/C1-8 Alkyl Acrylamide Copolymer, AMP-Acrylates/Diacetoneacrylamide Copolymer, AMP-Acrylates/Dimethylaminoethylmethacrylate Copolymer, *Bacillus*/Rice Bran Extract/Soybean Extract Ferment Filtrate, Bis-Butyloxyamodimethicone/PEG-60 Copolymer, Butyl Acrylate/Ethylhexyl Methacrylate Copolymer, Butyl Acrylate/Hydroxypropyl Dimethicone Acrylate Copolymer, Butylated PVP, Butyl Ester of Ethylene/MA Copolymer, Butyl Ester of PVM/MA Copolymer, Calcium/Sodium PVM/MA Copolymer, Corn Starch/Acrylamide/Sodium Acrylate Copolymer, Diethylene Glycolamine/Epichlorohydrin/Piperazine Copolymer, Dimethicone Crosspolymer, Diphenyl Amodimethicone, Ethyl Ester of PVM/MA Copolymer, Hydrolyzed Wheat Protein/PVP Crosspolymer, Isobutylene/Ethylmaleimide/Hydroxyethylmaleimide Copolymer, Isobutylene/MA Copolymer, Isobutylmethacrylate/Bis-Hydroxypropyl Dimethicone Acrylate Copolymer, Isopropyl Ester of PVM/MA Copolymer, Lauryl Acrylate Crosspolymer, Lauryl Methacrylate/Glycol Dimethacrylate Crosspolymer, MEA-Sulfite, Methacrylic Acid/Sodium Acrylamidomethyl Propane Sulfonate Copolymer, Methacryloyl Ethyl Betaine/Acrylates Copolymer, Octylacrylamide/Acrylates/Butylaminoethyl Methacrylate Copolymer, PEG/PPG-25/25 Dimethicone/Acrylates Copolymer, PEG-8/SMDI Copolymer, Polyacrylamide, Polyacrylate-6, Polybeta-Alanine/Glutaric Acid Crosspolymer, Polybutylene Terephthalate, Polyester-1, Polyethylacrylate, Polyethylene Terephthalate, Polymethacryloyl Ethyl Betaine, Polypentaerythrityl Terephthalate, Polyperfluoroperhydrophenanthrene, Polyquaternium-1, Polyquaternium-2, Polyquaternium-4, Polyquaternium-5, Polyquaternium-6, Polyquaternium-7, Polyquaternium-8, Polyquaternium-9, Polyquaternium-10, Polyquaternium-11, Polyquaternium-12, Polyquaternium-13, Polyquaternium-14, Polyquaternium-15, Polyquaternium-16, Polyquaternium-17, Polyquaternium-18, Polyquaternium-19, Polyquaternium-20, Polyquaternium-22, Polyquaternium-24, Polyquaternium-27, Polyquaternium-28, Polyquaternium-29, Polyquaternium-30, Polyquaternium-31, Polyquaternium-32, Polyquaternium-33, Polyquaternium-34, Polyquaternium-35, Polyquaternium-36, Polyquaternium-39, Polyquaternium-45, Polyquaternium-46, Polyquaternium-47, Polyquaternium-48, Polyquaternium-49, Polyquaternium-50, Polyquaternium-55, Polyquaternium-56, Polysilicone-9, Polyurethane-1, Polyurethane-6, Polyurethane-10, Polyvinyl Acetate, Polyvinyl Butyral, Polyvinylcaprolactam, Polyvinylformamide, Polyvinyl Imidazolinium Acetate, Polyvinyl Methyl Ether, Potassium Butyl Ester of PVM/MA Copolymer, Potassium Ethyl Ester of PVM/MA Copolymer, PPG-70 Polyglyceryl-10 Ether, PPG-12/SMDI Copolymer, PPG-51/SMDI Copolymer, PPG-10 Sorbitol, PVM/MA Copolymer, PVP, PVP/VA/Itaconic Acid Copolymer, PVP/VA/Vinyl Propionate Copolymer, Rhizobian Gum, Rosin Acrylate, Shellac, Sodium Butyl Ester of PVM/MA Copolymer, Sodium Ethyl Ester of PVM/MA Copolymer, Sodium Polyacrylate, Sterculia Urens Gum, Terephthalic Acid/Isophthalic Acid/Sodium Isophthalic Acid Sulfonate/Glycol Copolymer, Trimethylolpropane Triacrylate, Trimethylsiloxysilylcarbamoyl Pullulan, VA/Crotonates Copolymer, VA/Crotonates/Methacryloxybenzophenone-1 Copolymer, VA/Crotonates/Vinyl Neodecanoate Copolymer, VA/Crotonates/Vinyl Propionate Copolymer, VA/DBM Copolymer, VA/Vinyl Butyl Benzoate/Crotonates Copolymer, Vinylamine/Vinyl Alcohol Copolymer, Vinyl Caprolactam/VP/Dimethylaminoethyl Methacrylate Copolymer, VP/Acrylates/Lauryl Methacrylate Copolymer, VP/Dimethylaminoethylmethacrylate Copolymer, VP/DMAPA Acrylates Copolymer, VP/Hexadecene Copolymer, VP/VA Copolymer, VP/Vinyl Caprolactam/DMAPA Acrylates Copolymer, Yeast Palmitate and Styrene/VP Copolymer.

The polymer is particularly preferably selected from the group of amphoteric polymers. Most particularly preferred is the use of a copolymer of i) N-tert-octylacrylamide, ii) acrylic acid, iii) tert.-butylaminoethyl methacrylate and optionally further monomers Preferred amphoteric copolymers are preferably made up of at least about 90 wt %, preferably at least about 95 wt % and particularly at least about 97 wt % of the monomers N-tert-octylacrylamide, acrylic acid and tert.-butylaminoethyl methacrylate. Corresponding copolymers may also be obtained by using the monomers N-tert-octylacrylamide, acrylic acid and tert.-butylaminoethyl methacrylate exclusively.

Copolymers from the monomers N-tert-octylacrylamide, acrylic acid and tert.-butylaminoethyl methacrylate, methyl methacrylate and hydroxypropyl methacrylate are also preferred. It is most particularly preferred particularly when the copolymer is made up of at least about 90 wt %, preferably at least about 95 wt % and particularly at least about 97 wt % of the monomers N-tert-octylacrylamide, acrylic acid and tert.-butylaminoethyl methacrylate, methyl methacrylate and hydroxypropyl methacrylate.

The amphoteric copolymers described previously are marketed for example with the trade name Amphomer® (INCI name: Octylacrylamide/Acrylates/Butylaminoethyl Methacrylate Copolymer; CAS number 70801-07-9) by the company National Starch.

Particularly additional care substances may be cited as further active or auxiliary agents that may be contained as optional additives in the cosmetic compositions.

The product may contain as care substance for example at least one protein hydrolysate and/or one of the derivatives therefrom. Protein hydrolysates are product mixtures which are obtained by the acidically, basically or enzymatically catalyzed decomposition of proteins. As contemplated herein, the term protein hydrolysates is also understood to refer to total hydrolysates as well as individual amino acids and the derivatives thereof and mixtures of different amino acids. The molar weight of the protein hydrolysates usable as contemplated herein is between about 75, the molar weight of glycine, and about 200,000, the molar weight is preferably in the range from about 75 to about 50,000 and most particularly preferably from about 75 to about 20,000 Dalton.

The product as contemplated herein may further contain at least one vitamin, provitamin, vitamin precursor and/or one of the derivatives therefrom as a care substance. In this context, such vitamins, provitamins and vitamin precursors which are usually assigned to the groups A, B, C, E, F and H are preferred.

Further care substances are panthenol, caffeine, nicotinamide and sorbitol.

The products as contemplated herein may further contain at least plant extract, but also mono- and/or oligosaccharides and/or lipids as a care substance.

Aerosol dispensing containers are particularly suitable for the purpose of dispensing and applying the cosmetic compositions. Accordingly, a further object of the application relates to cosmetic products comprising
a) a cosmetic composition as contemplated herein
b) an aerosol dispensing container.

The term aerosol dispensing container is understood to refer to pressurized container in which a higher gas pressure prevails in the interior thereof than outside the container, and out of which a gas stream may be released via a valve. In other words, the aerosol dispensing container is a pressurized container by employing which a product (e.g., a cosmetic composition) may be discharged through a valve under the effect of the gas pressure inside the container.

The cosmetic products as contemplated herein may be manufactured in the usual way. As a result, all constituents of the cosmetic composition except the propellant are introduced into a suitable, pressure-resistant receptacle. This is then closed off with a valve. Finally, the desired quantity of propellant is introduced by conventional methods.

Receptacles made from metal (aluminum, tinplate, tin), reinforced and/or shatter-proof plastic or glass with an outer plastic coating are eligible for use as pressure-resistant containers, the selection factors for which include pressure- and breakage-resistance, corrosion resistance, ease of filling as well as visual considerations, manageability, printability etc. Special interior protection paints guarantee resistance to corrosion by the composition formed inside the pressurized container. It is particularly preferable if the valves used have an internally painted valve plate, wherein the paint coating and valve material must be compatible with each other. If aluminum valves are used, the valve plates thereof may be coated internally with Micoflex paint, for example. If tinplate valves are used as contemplated herein, their valve plates may be coated inside with PET (polyethylene terephthalate) for example.

A multichamber dispenser may also be used as the aerosol dispensing container. The Der multichamber dispenser may also be designed such that one chamber is filled with the compressed propellant and another chamber is contains the other constituents of the composition as contemplated herein. Such a multichamber dispenser is a receptacle also known as a bag-in-can package.

The spraying rate of the cosmetics products is preferably from about 6.5 to about 10.0 g/10 s.

As was noted earlier, the products as contemplated herein are particularly suitable for cleaning, revitalizing and deodorizing keratinous fibers. Corresponding uses of the cosmetic compositions are further objects of this Application.

A final object of this Application is a method for the temporary reshaping of keratinous fibers, particularly human hair, in which a cosmetic composition as contemplated herein is applied to keratinous fibers. The notes given previously regarding the constituents of said composition, their proportions by weight and preferred embodiments thereof apply mutatis mutandis for said method.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A cosmetic composition for cosmetic treatment of keratinous fibers, comprising:
   (a) from about 0.1 to about 5.0 wt % fibers, wherein the fibers are selected from the group consisting of flax fibers, kapok fibers, and combinations thereof;
   (b) from about 5.0 to about 19 wt % ethanol; and
   (c) from about 78 to about 94 wt % propellant.

2. The cosmetic composition according to claim 1, further comprising:
   (d) from about 0.05 to about 9 wt % dye(s); and
   (e) from about 0.05 to about 9 wt % pigment(s);
   with the qualification that the sum of the quantities of the substances (d) and (e) is equal to from about 0.0001 to about 10 wt % relative to the total weight of the cosmetic composition.

3. The cosmetic composition according to claim 1, wherein the proportion by weight of the fibers is from about 0.1 to about 2.0 wt % relative to the total weight of the cosmetic composition.

4. The cosmetic composition according to claim 1, wherein the fibers are flax fibers.

5. The cosmetic composition according to claim 1, wherein the fibers are kapok fibers.

6. The cosmetic composition according to claim 1, wherein the proportion by weight of the ethanol is from about 7.0 to about 17 wt % of the total weight of the cosmetic composition.

7. The cosmetic composition according to claim 1, wherein the composition comprises at least one starch compound as a further constituent.

8. The cosmetic composition according to claim 1, wherein the composition comprises a starch compound which constitutes from about 1.0 to about 10 wt % relative to the total weight thereof.

9. The cosmetic composition according to claim 8, wherein the starch compound is a starch-pigment compound.

10. The cosmetic composition according to claim 8, wherein the starch comprises a starch-pigment compound and a starch-dye compound.

11. The cosmetic composition according to claim 2, wherein the cosmetic composition comprises at least one pigment from the group CI12490, CI14700, CI14720, CI15510, CI15985, CI45380, CI47005, CI60730, CI61565, CI73360, CI74160, CI77007, CI77019, CI77288, CI77289, CI77491, CI77492, wherein the total quantity of pigment(s) from this group constitutes from about 0.25 to about 8 wt %, relative to the total weight of the cosmetic composition.

12. The cosmetic composition according to claim 1, wherein the fibers comprise a fiber-dye compound.

13. The cosmetic composition according to claim 1, wherein the fibers comprise a fiber-dye compound and a fiber-pigment compound.

14. A cosmetic product, comprising
   a) a cosmetic composition according to claim 1; and
   b) an aerosol dispensing container.

15. The cosmetic composition according to claim 1, wherein the proportion by weight of the fibers is from about 0.1 to about 0.5 wt % relative to the total weight of the cosmetic composition.

16. The cosmetic composition according to claim 1, wherein the fibers are hydrophobized with a paraffin, a wax, or a combination thereof.

17. The cosmetic composition according to claim 1, wherein the proportion by weight of the ethanol is from about 10 to about 14 wt % relative to the total weight of the cosmetic composition.

18. The cosmetic composition according to claim 1, wherein the composition comprises a starch compound which constitutes from about 3.0 to about 5 wt % relative to the total weight of thereof.

19. The cosmetic composition according to claim 2, wherein the cosmetic composition comprises from about 0.25 to about 8 wt % dye relative to the total weight thereof.

20. The cosmetic composition according to claim 1,
   wherein the proportion by weight of the fibers is from about 0.1 to about 0.5 wt % relative to the total weight of the cosmetic composition;
   wherein the proportion by weight of the ethanol is from about 10 to about 14 wt % of the total weight of the cosmetic composition;
   wherein the composition comprises at least one starch compound as a further constituent;
   wherein the starch compound constitutes from about 3.0 to about 5 wt % relative to the total weight thereof;
   wherein the composition comprises from about 0.25 to about 8 wt % dye(s), relative to the total weight thereof;
   wherein the composition comprises from about 0.25 to about 8 wt % pigment(s), relative to the total weight thereof; and
   wherein the pigment is chosen from the group of CI12490, CI14700, CI14720, CI15510, CI15985, CI45380, CI47005, CI60730, CI61565, CI73360, CI74160, CI77007, CI77019, CI77288, CI77289, CI77491, and CI77492.

* * * * *